(12) United States Patent
Matsumoto (10) Patent No.: US 11,116,481 B2
(45) Date of Patent: Sep. 14, 2021

(54) ULTRASOUND DIAGNOSTIC APPARATUS AND CONTROL METHOD OF ULTRASOUND DIAGNOSTIC APPARATUS

(71) Applicant: FUJIFILM Corporation, Tokyo (JP)

(72) Inventor: Tsuyoshi Matsumoto, Ashigara-kami-gun (JP)

(73) Assignee: FUJIFILM Corporation, Tokyo (JP)

(*) Notice: Subject to any disclaimer, the term of this patent is extended or adjusted under 35 U.S.C. 154(b) by 357 days.

(21) Appl. No.: 16/294,749

(22) Filed: Mar. 6, 2019

(65) Prior Publication Data
US 2019/0216441 A1 Jul. 18, 2019

Related U.S. Application Data

(63) Continuation of application No. PCT/JP2017/020928, filed on Jun. 6, 2017.

(30) Foreign Application Priority Data

Sep. 21, 2016 (JP) .............................. JP2016-184049

(51) Int. Cl.
| | |
|---|---|
| *A61B 8/00* | (2006.01) |
| *G06T 7/00* | (2017.01) |
| *G06T 7/246* | (2017.01) |
| *A61B 8/08* | (2006.01) |
| *G06K 9/62* | (2006.01) |

(52) U.S. Cl.
CPC .............. *A61B 8/54* (2013.01); *A61B 8/0833* (2013.01); *A61B 8/4254* (2013.01);
(Continued)

(58) Field of Classification Search
CPC .............. G06K 9/6204; G06K 9/6215; G06K 2209/057; G06T 7/0012; G06T 7/246;
(Continued)

(56) References Cited

U.S. PATENT DOCUMENTS

| | | | |
|---|---|---|---|
| 9,674,447 B2 * | 6/2017 | Kam | .................. H04N 5/23293 |
| 10,198,668 B2 * | 2/2019 | Ryu | ...................... G06K 9/6267 |

(Continued)

FOREIGN PATENT DOCUMENTS

| | | |
|---|---|---|
| JP | 2007-301398 A | 11/2007 |
| JP | 2011-110431 A | 6/2011 |

(Continued)

OTHER PUBLICATIONS

Extended European Search Report dated Sep. 2, 2019, for corresponding European Application No. 17852622.4.

(Continued)

*Primary Examiner* — Joel Lamprecht (74) *Attorney, Agent, or Firm* — Birch, Stewart, Kolasch & Birch, LLP (57) ABSTRACT

An ultrasound diagnostic apparatus includes: an image acquisition unit that acquires an ultrasound image by transmitting an ultrasound beam from an ultrasound probe toward a subject and receiving an ultrasound beam reflected from the subject; an image analysis unit that analyzes the acquired ultrasound image; and a movement amount detection unit that detects a movement amount of the ultrasound probe. The image analysis unit performs image analysis on an ultrasound image of a single frame in a case where the movement amount of the ultrasound probe is equal to or greater than a threshold value, and performs image analysis on ultrasound images of a plurality of frames in a case where the movement amount of the ultrasound probe is less than the threshold value.

19 Claims, 3 Drawing Sheets

(52) U.S. Cl.
CPC .......... *A61B 8/5238* (2013.01); *G06K 9/6204* (2013.01); *G06K 9/6215* (2013.01); *G06T 7/0012* (2013.01); *G06T 7/246* (2017.01); *A61B 8/4245* (2013.01); *A61B 8/4427* (2013.01); *A61B 8/485* (2013.01); *A61B 8/486* (2013.01); *A61B 8/488* (2013.01); *A61B 8/5223* (2013.01); *A61B 8/5276* (2013.01); *G06K 2209/057* (2013.01); *G06T 2207/10132* (2013.01)

(58) Field of Classification Search
CPC ............ G06T 2207/10132; A61B 8/54; A61B 8/4254; A61B 8/5238; A61B 8/0833; A61B 8/4427; A61B 8/485; A61B 8/4245; A61B 8/486; A61B 8/5223; A61B 8/488; A61B 8/5276
See application file for complete search history.

(56) References Cited

U.S. PATENT DOCUMENTS

| | | |
|---|---|---|
| 2011/0125018 A1 | 5/2011 | Shin et al. |
| 2014/0155749 A1 | 6/2014 | Ogasawara |
| 2014/0213901 A1 | 7/2014 | Shackelford |
| 2015/0164482 A1 | 6/2015 | Toji |
| 2015/0310581 A1 | 10/2015 | Radulescu et al. |
| 2016/0019441 A1 | 1/2016 | Ryu et al. |
| 2016/0048737 A1 | 2/2016 | Kam et al. |
| 2017/0258451 A1 | 9/2017 | Sakanashi et al. |

FOREIGN PATENT DOCUMENTS

| | | |
|---|---|---|
| JP | 2015-131100 A | 7/2015 |
| JP | 2016-501605 A | 1/2016 |
| WO | WO 2016/088758 A1 | 6/2016 |

OTHER PUBLICATIONS

International Preliminary Report on Patentability and Written Opinion of the International Searching Authority (Forms PCT/IB/326, PCT/IB/373, and PCT/ISA/237) for International Application No. PCT/JP2017/020928, dated Apr. 4, 2019, with English translation.
International Search Report (Form PCT/ISA/210) for International Application No. PCT/JP2017/020928 dated Aug. 22, 2017, with English translation.

* cited by examiner

ULTRASOUND DIAGNOSTIC APPARATUS AND CONTROL METHOD OF ULTRASOUND DIAGNOSTIC APPARATUS

CROSS-REFERENCE TO RELATED APPLICATIONS

This application is a Continuation of PCT International Application No. PCT/JP2017/020928 filed on Jun. 6, 2017, which claims priority under 35 U.S.C. § 119(a) to Japanese Patent Application No. 2016-184049 filed on Sep. 21, 2016. The above application is hereby expressly incorporated by reference, in its entirety, into the present application.

BACKGROUND OF THE INVENTION

1. Field of the Invention

The present invention relates to an ultrasound diagnostic apparatus and a control method of an ultrasound diagnostic apparatus and in particular, to an ultrasound diagnostic apparatus for determining a part of a subject whose ultrasound image is generated.

2. Description of the Related Art

Conventionally, an ultrasound diagnostic apparatus is known as an apparatus that obtains an image of the inside of a subject by applying a transducer array to the subject. A general ultrasound diagnostic apparatus acquires element data by transmitting an ultrasound beam from a transducer array, in which a plurality of elements are arranged, to the inside of a subject and receiving ultrasound echoes from the subject in the transducer array. Then, the ultrasound diagnostic apparatus electrically processes the obtained element data to obtain an ultrasound image of the relevant part of the subject.

In such an ultrasound diagnostic apparatus, it is possible to detect the movement of an ultrasound probe and easily and quickly perform ultrasound diagnosis by using the detection result. For example, JP2016-501605A discloses an ultrasound diagnostic apparatus that detects the movement of an ultrasound probe and acquires an ultrasound image, determines a diagnostic part, and analyzes the ultrasound image in a case where it is determined that the ultrasound probe is stationary based on the detection result.

SUMMARY OF THE INVENTION

Incidentally, for example, in the extended Focused Assessment with Sonography for Trauma (eFAST) examination for examining a plurality of diagnostic parts continuously for initial examination of an injured patient in emergency, it is requested to quickly perform ultrasound examination on the plurality of diagnostic parts. For this reason, for example, in the eFAST examination, there is a problem that it is difficult to precisely determine diagnostic parts since the amount of information for determining each diagnostic part, which is obtained from the generated ultrasound image, is small.

In the technique disclosed in JP2016-501605A, there is a problem that it is not possible to determine the diagnostic part and analyze the ultrasound image in a case where the ultrasound probe is moving. In addition, in the technique disclosed in JP2016-501605A, there is a problem that it is difficult to select an appropriate image analysis method for the diagnostic part.

The present invention has been made in order to solve such conventional problems, and it is an object of the present invention to provide an ultrasound diagnostic apparatus and a control method of an ultrasound diagnostic apparatus capable of selecting an image analysis method based on the movement of an ultrasound probe and precisely determining a diagnostic part.

In order to achieve the aforementioned object, an ultrasound diagnostic apparatus of the present invention comprises: an ultrasound probe; an image acquisition unit that acquires an ultrasound image by transmitting an ultrasound beam from the ultrasound probe toward a subject and receiving an ultrasound beam reflected from the subject; an image analysis unit that analyzes the ultrasound image acquired by the image acquisition unit; and a movement amount detection unit that detects a movement amount of the ultrasound probe. The image analysis unit performs image analysis on an ultrasound image of a single frame in a case where the movement amount of the ultrasound probe detected by the movement amount detection unit is equal to or greater than a predetermined threshold value, and performs image analysis on ultrasound images of a plurality of frames in a case where the movement amount of the ultrasound probe detected by the movement amount detection unit is less than the predetermined threshold value.

It is preferable that the image analysis unit performs image analysis including pattern recognition or pixel value analysis on the ultrasound image of the single frame as the image analysis on the ultrasound image of the single frame.

It is preferable that the image analysis unit performs analysis on a movement of a specific pattern commonly included in the ultrasound images of the plurality of frames as the image analysis on the ultrasound images of the plurality of frames.

Alternatively, the image analysis unit may perform image analysis for each frame on the ultrasound images of the plurality of frames acquired in time series by the image acquisition unit, as the image analysis on the ultrasound images of the plurality of frames, and integrate results of the image analyses.

It is preferable to further comprise a part determination unit that determines a part of the subject, which is included in each ultrasound image on which the image analysis has been performed, based on a result of the image analysis of the image analysis unit.

It is preferable that the movement amount detection unit comprises a motion sensor attached to the ultrasound probe and the motion sensor detects an acceleration, an angular speed, or a position of the ultrasound probe.

Alternatively, the movement amount detection unit may comprise a motion sensor provided away from the ultrasound probe, and the motion sensor may detect a position of the ultrasound probe.

A control method of an ultrasound diagnostic apparatus of the present invention comprises: acquiring an ultrasound image by transmitting an ultrasound beam from an ultrasound probe toward a subject and receiving an ultrasound beam reflected from the subject; analyzing the acquired ultrasound image; and detecting a movement amount of the ultrasound probe. Image analysis is performed on an ultrasound image of a single frame in a case where the detected movement amount of the ultrasound probe is equal to or greater than a predetermined threshold value, and image analysis is performed on ultrasound images of a plurality of frames in a case where the detected movement amount of the ultrasound probe is less than the predetermined threshold value.

According to the present invention, the ultrasound diagnostic apparatus has the image analysis unit that performs image analysis on the ultrasound image of the single frame or image analysis on the ultrasound images of the plurality of frames based on the movement amount of the ultrasound probe. Therefore, it is possible to precisely determine a diagnostic part according to the movement of the ultrasound probe.

DESCRIPTION OF THE PREFERRED EMBODIMENTS

Hereinafter, an embodiment of the present invention will be described with reference to the accompanying diagrams.

First Embodiment

Figure 1:
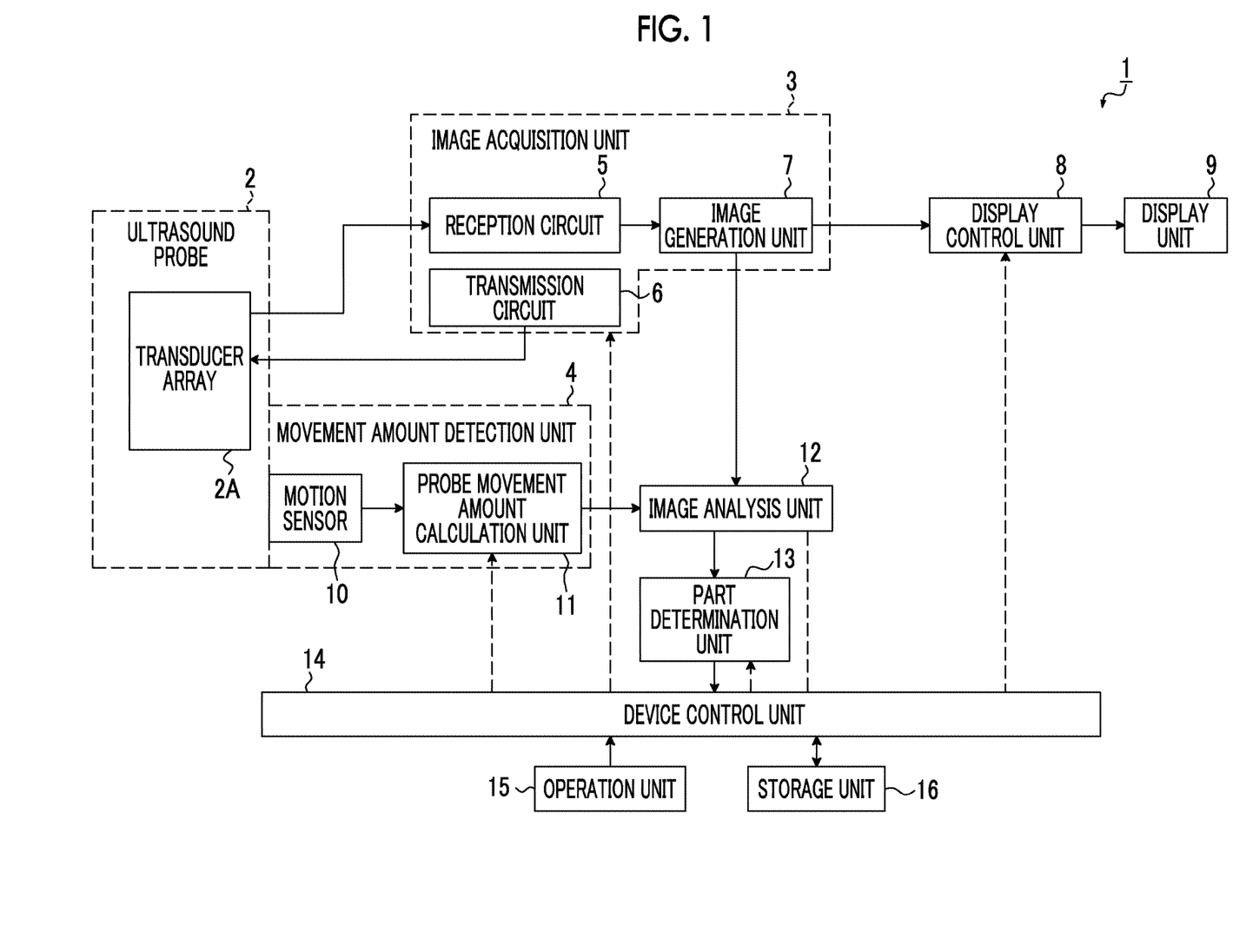
FIG. 1 is a block diagram showing the configuration of an ultrasound diagnostic apparatus according to a first embodiment of the present invention.

FIG. 1 shows the configuration of an ultrasound diagnostic apparatus according to a first embodiment of the present invention. An ultrasound diagnostic apparatus 1 includes an ultrasound probe 2 including a transducer array 2A built thereinto, and a display control unit 8 and a display unit 9 are sequentially connected to the ultrasound probe 2 through an image acquisition unit 3.

The image acquisition unit 3 has a reception circuit 5 and a transmission circuit 6, which are connected to the transducer array 2A of the ultrasound probe 2, and an image generation unit 7 connected to the reception circuit 5, and the display control unit 8 is connected to the image generation unit 7. The image generation unit 7 is connected to an image analysis unit 12. The ultrasound probe 2 comprises a motion sensor 10, and the motion sensor 10 is connected to a probe movement amount calculation unit 11. The image analysis unit 12 is connected to the probe movement amount calculation unit 11, and a part determination unit 13 is connected to the image analysis unit 12. The motion sensor 10 and the probe movement amount calculation unit 11 configure a movement amount detection unit 4.

A device control unit 14 is connected to the image acquisition unit 3, the display control unit 8, the probe movement amount calculation unit 11, the image analysis unit 12, and the part determination unit 13, and an operation unit 15 and a storage unit 16 are connected to the device control unit 14. The device control unit 14 and the storage unit 16 are connected to each other so that information can be transmitted and received bidirectionally.

The transducer array 2A of the ultrasound probe 2 shown in FIG. 1 has a plurality of elements (ultrasound transducer) arranged in a one-dimensional or two-dimensional manner. Each of the elements transmits an ultrasound wave according to a driving signal supplied from the transmission circuit 6 and receives an ultrasound echo from the subject, and outputs the reception signal. For example, each element is formed by using a transducer in which electrodes are formed at both ends of a piezoelectric body formed of piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like.

In a case where a pulsed or continuous-wave voltage is applied to the electrodes of such a transducer, the piezoelectric body expands and contracts to generate pulsed or continuous-wave ultrasound waves from each transducer. From the combined wave of these ultrasound waves, an ultrasound beam is formed. The respective transducers expand and contract by receiving the propagating ultrasound waves, thereby generating electrical signals. These electrical signals are output, as reception signals of the ultrasound waves, from each transducer to the reception circuit 5.

Figure 2:
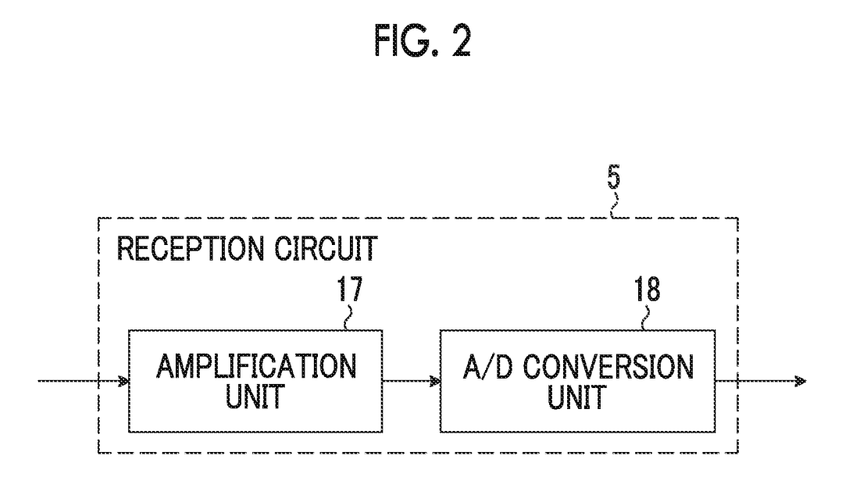
FIG. 2 is a block diagram showing the internal configuration of a reception circuit shown in FIG. 1.

As shown in FIG. 2, the reception circuit 5 of the image acquisition unit 3 has a configuration in which an amplification unit 17 and an analog/digital (A/D) conversion unit 18 are connected in series to each other. In the reception circuit 5, the amplification unit 17 amplifies the reception signal output from each element of the transducer array 2A, and the A/D conversion unit 18 converts the amplified signal into a digital signal to obtain element data and outputs the obtained element data to the image generation unit 7.

The transmission circuit 6 of the image acquisition unit 3 includes, for example, a plurality of pulse generators. Based on a transmission delay pattern selected according to the control signal from the device control unit 14, the transmission circuit 6 adjusts the amount of delay of each driving signal so that ultrasound waves transmitted from the plurality of elements of the transducer array 2A form an ultrasound beam, and supplies the obtained signals to the plurality of elements.

Figure 3:
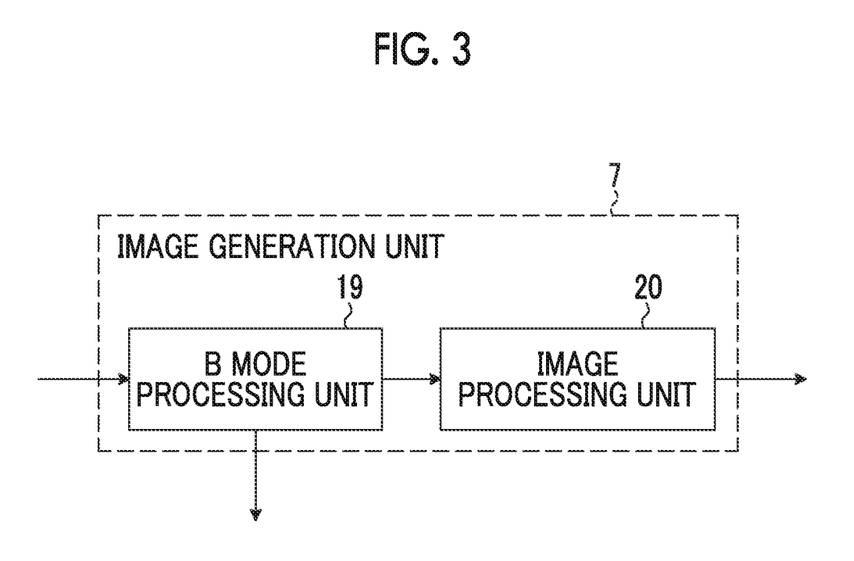
FIG. 3 is a block diagram showing the internal configuration of an image generation unit shown in FIG. 1.

As shown in FIG. 3, the image generation unit 7 of the image acquisition unit 3 has a configuration in which a brightness mode (B mode) processing unit 19 and an image processing unit 20 are sequentially connected in series to each other.

Based on the reception delay pattern selected according to the control signal from the device control unit 14, the B mode processing unit 19 performs reception focusing processing in which delays are given to respective pieces of element data according to the set sound speed and addition (phasing addition) is performed. Through the reception focusing processing, a sound ray signal with narrowed focus of the ultrasound echo is generated. The B mode processing unit 19 generates a B mode image signal, which is tomographic image information regarding tissues inside the subject, by correcting the attenuation of the sound ray signal due to the propagation distance according to the depth of the reflection position of the ultrasound wave and then performing envelope detection processing. The B mode image signal generated by the B mode processing unit 19 is output to the display control unit 8 or the image analysis unit 12.

The image processing unit 20 converts (raster conversion) the B mode image signal generated by the B mode processing unit 19 into an image signal according to the normal television signal scanning method and performs various kinds of required image processing, such as gradation processing, on the B mode image signal, and then outputs the B mode image signal to the display control unit 8.

As shown in FIG. 1, the display control unit 8 of ultrasound diagnostic apparatus 1 displays an ultrasound diagnostic image on the display unit 9 based on the B mode image signal acquired by the image acquisition unit 3.

The display unit 9 includes, for example, a display device, such as a liquid crystal display (LCD), and displays an ultrasound diagnostic image under the control of the device control unit 14.

The ultrasound probe 2 comprises the motion sensor 10 of the movement amount detection unit 4 that detects, as an electrical signal, the motion or the position of the ultrasound probe 2 operated by the operator during the ultrasound diagnosis.

The motion sensor 10 is not particularly limited as long as it is possible to detect the motion or the position of the ultrasound probe 2, but a case where an acceleration sensor for detecting the motion of the ultrasound probe 2 is used as the motion sensor 10 will be described below. In this case, the motion sensor 10 detects, as an electrical signal, the acceleration of three components along three axes perpendicular to each other in the three-dimensional space. The signal detected by the motion sensor 10 is output to the probe movement amount calculation unit 11 of the movement amount detection unit 4.

Based on a signal indicating the motion of the ultrasound probe 2 detected by the motion sensor 10, the probe movement amount calculation unit 11 of the movement amount detection unit 4 calculates the movement amount of the ultrasound probe 2 that is an index of the movement of the ultrasound probe 2 during the ultrasound diagnosis. For example, after calculating the posture angle of the ultrasound probe 2 from the acceleration in the three-dimensional space obtained by the motion sensor 10 for each frame of the ultrasound image using a known calculation method, the time change amount of the posture angle between frames can be calculated as the movement amount of the ultrasound probe 2 using the plurality of calculated posture angles. For example, as the time change amount of the posture angle of the ultrasound probe 2, the probe movement amount calculation unit 11 can calculate a standard deviation with respect to the posture angle calculated for each predetermined number of ultrasound images acquired in time series by the image acquisition unit 3. In this case, it is preferable that the plurality of calculated posture angles only increase in time series or only decrease in time series, and it is preferable that the acquisition time interval between ultrasound images of a plurality of frames used for calculation of the movement amount of the ultrasound probe 2 is sufficiently short.

The image analysis unit 12 performs image analysis, such as movement analysis and pattern recognition, on the B mode image signal generated by the B mode processing unit 19 of the image generation unit 7 of the image acquisition unit 3, and outputs the image analysis result to the part determination unit 13. In a case where the movement amount of the ultrasound probe 2 calculated by the probe movement amount calculation unit 11 of the movement amount detection unit 4 is equal to or greater than a predetermined threshold value, the image analysis unit 12 performs image analysis on the ultrasound image of a single frame. In a case where the movement amount of the ultrasound probe 2 is less than the predetermined threshold value, the image analysis unit 12 performs image analysis on the ultrasound image of a plurality of frames.

Based on the analysis result of the ultrasound image by the image analysis unit 12, the part determination unit 13 determines the part of the subject included in the ultrasound image, and outputs information of the determined part to the device control unit 14.

The device control unit 14 controls each unit of the ultrasound diagnostic apparatus 1 based on a command input by the operator through the operation unit 15. In addition, the device control unit 14 changes the imaging conditions at the time of acquiring the ultrasound image to imaging conditions suitable for the part determined by the part determination unit 13.

The operation unit 15 is for the operator to perform an input operation, and can be configured to comprise a keyboard, a mouse, a trackball, a touch panel, and the like.

The storage unit 16 stores an operation program and the like of the ultrasound diagnostic apparatus 1, and recording media, such as a hard disc drive (HDD), a solid state drive (SSD), a flexible disc (FD), a magneto-optical disc (MO), a magnetic tape (MT), a random access memory (RAM), a compact disc (CD), a digital versatile disc (DVD), a secure digital card (SD card), and a universal serial bus memory (USB memory), or a server can be used.

The image generation unit 7 of the image acquisition unit 3, the display control unit 8, the probe movement amount calculation unit 11 of the movement amount detection unit 4, the image analysis unit 12, the part determination unit 13, and the device control unit 14 are configured by a central processing unit (CPU) and an operation program causing the CPU to execute various kinds of processing. However, these may also be configured by digital circuits. The image generation unit 7, the display control unit 8, the probe movement amount calculation unit 11, the image analysis unit 12, the part determination unit 13, and the device control unit 14 can also be integrated partially or entirely in one CPU.

Figure 4:
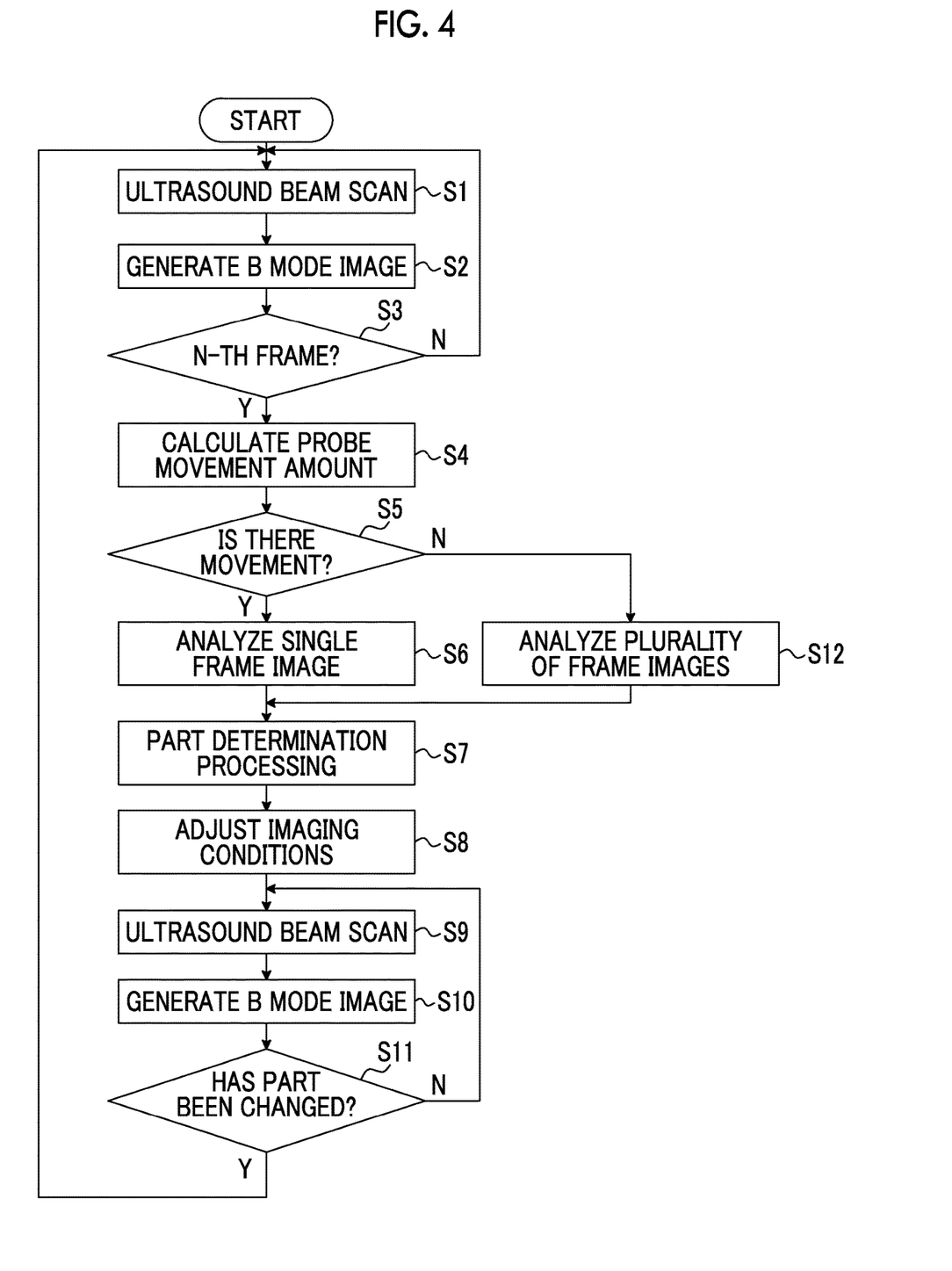
FIG. 4 is a flowchart relevant to the operation of the ultrasound diagnostic apparatus of the present invention.

Next, the operation of the ultrasound diagnostic apparatus 1 in the first embodiment will be described with reference to the flowchart shown in FIG. 4.

First, in step S1, under the predetermined imaging conditions, scanning and transmission and reception of ultrasound beams using a plurality of ultrasound transducers of the transducer array 2A of the ultrasound probe 2 are performed by the reception circuit 5 and the transmission circuit 6 of the image acquisition unit 3. In this case, a reception signal is output to the reception circuit 5 from each ultrasound transducer that has received the ultrasound echo from the subject, and amplification and A/D conversion of the reception signal are performed by the amplification unit 17 and the A/D conversion unit 18 of the reception circuit 5 to generate a reception signal. In a case where scanning and transmission and reception of ultrasound beams are performed, the motion sensor 10 of the movement amount detection unit 4 detects the motion of the ultrasound probe 2 scanned by the operator as an electrical signal. The imaging conditions set as the initial value, which are used in step S1, are, for example, imaging conditions in which general settings are made for a plurality of diagnostic parts. Such general imaging conditions for a plurality of diagnostic parts are often set so that a plurality of parts can be quickly examined in continuous diagnosis, such as eFAST examination, for example.

In step S2, the reception signal is input to the image generation unit 7, and a B mode image signal is generated by the B mode processing unit 19 of the image generation unit 7.

In step S3, the device control unit 14 determines whether or not an ultrasound image of the N-th frame counted from the start of the ultrasound examination on each part of the subject has been acquired. Here, N is a natural number of 2 or more. In a case where it is determined that the acquired ultrasound image is less than N frames in step S3, the process returns to step S1 and the ultrasound image is acquired again in steps S1 and S2.

In a case where it is determined that the ultrasound image of the N-th frame has been acquired in step S3, the process proceeds to step S4. In step S4, the probe movement amount calculation unit 11 of the movement amount detection unit 4 calculates the posture angle of the ultrasound probe 2 at the time of scanning or transmission and reception of ultrasound beams performed in step S1 based on the electrical signal indicating the motion of the ultrasound probe 2 input from the motion sensor 10, and then calculates the time change amount of the posture angle between the frames. For example, first, from the acceleration of three components along three axes perpendicular to each other in the three-dimensional space that is detected by the motion sensor 10, the probe movement amount calculation unit 11 can calculate the posture angle of the ultrasound probe 2 for each frame with respect to ultrasound images of a plurality of frames using a known calculation method. Then, as the movement amount of the ultrasound probe 2, for example, the standard deviation of the plurality of calculated posture angles can be calculated by the probe movement amount calculation unit 11.

In step S5, the image analysis unit 12 determines whether or not the movement amount of the ultrasound probe 2 calculated in step S4 is equal to or greater than a predetermined threshold value. That is, in step S5, the image analysis unit 12 determines whether or not the ultrasound probe 2 has been moved by the operator at the time of ultrasound diagnosis by performing determination using a threshold value for the movement amount of the ultrasound probe 2. The threshold value can be determined, for example, by calculating a statistical value for the movement amount of the ultrasound probe 2 in past diagnosis or preliminary test or the like.

In a case where it is determined that the calculated movement amount of the ultrasound probe 2 is equal to or greater than the predetermined threshold value in step S5, the process proceeds to step S6. In a case where the ultrasound probe 2 moves a lot by the operator at the time of ultrasound diagnosis, the movement of the part itself of the subject, such as beating of the heart, in the ultrasound images of a plurality of frames is hidden by the movement of the ultrasound probe 2. Therefore, in step S6, the image analysis unit 12 performs image analysis on an ultrasound image of a single frame among the ultrasound images of a plurality of frames acquired by the image acquisition unit 3. Image analysis on the ultrasound image of a single frame can be performed using various methods. For example, pattern recognition, such as template matching, can be performed to calculate the similarity between the part included in the ultrasound image and the template of a plurality of parts as a score.

In step S7 subsequent to step S6, the part determination unit 13 determines the part included in the ultrasound image based on the result of the image analysis on the ultrasound image of a single frame in step S6. For example, in a case where template matching is performed as the image analysis on the ultrasound image of a single frame in step S6, the part can be determined by determining whether or not the calculated score of the similarity is equal to or greater than a predetermined value.

In step S8, the device control unit 14 changes the imaging conditions to imaging conditions suitable for the part determined by the part determination unit 13.

Then, in step S9, the reception circuit 5 and the transmission circuit 6 of the image acquisition unit 3 perform scanning and transmission and reception of ultrasound beams with respect to the part determined by the part determination unit 13 using the imaging conditions changed in step S8.

Then, in step S10, the image generation unit 7 of the image acquisition unit 3 generates a B mode image signal from the reception signal acquired by the reception circuit 5 and the transmission circuit 6 using the imaging conditions changed in step S8.

In step S11, the device control unit 14 determines whether or not the part of the subject under ultrasound examination currently has been changed. For example, in a case where the diagnostic part moves from the heart to the lung, it is determined that the diagnostic part has been changed. Specifically, in general, in a case where the diagnostic part is changed, the probe is away from the body surface to become in an aerial radiation state. By detecting such an aerial radiation state (a state in which a reflected signal cannot be obtained), it is possible to determine the change of the diagnostic part. In a case where it is determined that the diagnostic part is not changed, that is, the same diagnostic part is examined in step S11, the process returns to step S9 and the acquisition of the ultrasound image using the imaging conditions changed in step S8 is performed again. On the other hand, in a case where it is determined that the diagnostic part has been changed in step S11, the process returns to step S1. Thereafter, in a case where the process proceeds to step S3 through step S2, it is determined whether or not the ultrasound image acquired for a new diagnostic part is the N-th frame.

In a case where it is determined that the movement amount of the ultrasound probe 2 calculated in step S4 is equal to or less than the predetermined threshold value in step S5, the process proceeds to step S12. In a case where the movement of the ultrasound probe 2 by the operator is small at the time of ultrasound diagnosis, the movement of the part itself of the subject, such as beating of the heart, in the ultrasound images of a plurality of frames is hardly affected by the movement of the ultrasound probe 2. Therefore, in step S12, the image analysis unit 12 performs image analysis on a plurality of frame acquired by the image acquisition unit 3, that is, ultrasound images of N frames. The image analysis on ultrasound images of a plurality of frames can be performed using various methods. For example, a time-series image analysis method called an optical flow can be used. Although not shown, the optical flow is a method in which ultrasound images of frames adjacent to each other in the order of time series acquired by the image acquisition unit 3 are used and, for a plurality of characteristic patterns in the same part commonly included in the ultrasound images, a movement direction and a distance of each pattern are mapped using a vector or the like. The image analysis unit 12 can calculate the number of vectors (vector number) mapped to the ultrasound image by the optical flow.

In step S7 subsequent to step S12, the part determination unit 13 determines the part included in the ultrasound image based on the analysis result of the ultrasound images of a plurality of frame in step S12. For example, in a case where image analysis using an optical flow is performed in step S12, the part can be determined by determining whether or not the vector number calculated in step S12 is equal to or greater than a predetermined value. As described above, in a case where the movement amount of the ultrasound probe 2 is small, for example, a part with a lot of movement, such as the heart, and a part with little movement, such as the abdomen, can be easily determined by determining the part using the time-series analysis method.

As described above, according to the ultrasound diagnostic apparatus 1 of the present invention shown in FIG. 1, the movement amount of the ultrasound probe 2 is detected, and image analysis on the ultrasound image of a single frame or image analysis on the ultrasound images of a plurality of frames is performed according to whether or not the movement amount is equal to or greater than a predetermined threshold value. The ultrasound diagnostic apparatus 1 determines a part included in the ultrasound image using the image analysis result, and acquires an ultrasound image again using the imaging conditions suitable for the determined part. As described above, since the ultrasound diagnostic apparatus 1 according to the embodiment of the present invention can select an image analysis method for determining a part included in the ultrasound image based on the movement amount of the ultrasound probe 2, it is possible to quickly determine the part and improve the accuracy in determining the part.

In the above description, in step S3, it is determined whether or not an ultrasound image of the N-th frame counted from the start of the ultrasound examination on each part of the subject has been acquired. However, the frame number N that is the threshold value of the determination may be input by the operator through the operation unit 15 before the diagnosis by the ultrasound diagnostic apparatus 1 is started, or may be included in the operation program of the ultrasound diagnostic apparatus 1.

Step S3 is a trigger for proceeding to step S4. However, as long as ultrasound images of two or more frames are acquired before proceeding to step S4 for calculating the movement amount of the ultrasound probe 2, the determination performed in step S3 is not limited to the above-described example. For example, although not shown, in step S3, the device control unit 14 can determine whether or not a predetermined time has passed from the start of ultrasound examination on each part of the subject. In this case, the ultrasound diagnostic apparatus 1 repeats the acquisition of the ultrasound image by repeating steps S1 to S3 until a predetermined time passes, and proceeds to step S4 in a case where the predetermined time has passed. The predetermined time may be input by the operator through the operation unit 15 before the diagnosis by the ultrasound diagnostic apparatus 1 is started, or may be included in the operation program of the ultrasound diagnostic apparatus 1.

As another example, although not shown, in step S3, the device control unit 14 can determine whether or not ultrasound images of a predetermined number of frames counted from the start of ultrasound examination on each part of the subject have been acquired. In this case, the ultrasound diagnostic apparatus 1 repeats the acquisition of the ultrasound image by repeating steps S1 to S3 until ultrasound images of a predetermined number of frames counted from the start of ultrasound examination on each part of the subject are acquired. Then, in a case where it is determined that ultrasound images of a predetermined number of frames have been acquired in step S3, the process proceeds to step S4. The predetermined number of frames may be input by the operator through the operation unit 15 before the diagnosis by the ultrasound diagnostic apparatus 1 is started, or may be included in the operation program of the ultrasound diagnostic apparatus 1.

The method of calculating the posture angle in the probe movement amount calculation unit 11 of the movement amount detection unit 4 is not limited to the method described above as long as it is possible to calculate the posture angle of the ultrasound probe 2. For example, although not shown, the probe movement amount calculation unit 11 may calculate the posture angle of the ultrasound probe 2 based on the position information of the ultrasound probe 2 calculated by time-integrating the acceleration detected by the motion sensor 10 twice within a predetermined time.

As the motion sensor 10 for detecting the movement amount of the ultrasound probe 2, an acceleration sensor is used. However, other sensors may be used as the motion sensor 10 as long as the sensors detect the motion or the position of the ultrasound probe 2. As such a motion sensor 10, in addition to the acceleration sensor, for example, a gyro sensor, a magnetic sensor, or a global positioning system (GPS) sensor can be used. These sensors may be mounted on the ultrasound probe 2 or may be built into the ultrasound probe 2.

For example, by using a gyro sensor attached to the ultrasound probe 2 as the motion sensor 10, the posture angle of the ultrasound probe 2 can be detected by a known calculation method based on the angular speed of the ultrasound probe 2 obtained from the gyro sensor. For example, by using a magnetic sensor as the motion sensor 10, the posture angle of the ultrasound probe 2 may be detected based on the position information of the ultrasound probe 2 detected by the magnetic sensor. In addition, for example, by using a GPS sensor as the motion sensor 10, the posture angle of the ultrasound probe 2 can be detected based on the position information of the ultrasound probe 2 obtained from the GPS sensor.

As long as the motion or the position of the ultrasound probe 2 is detected, the motion sensor 10 may not be attached to or built into the ultrasound probe 2 or may be provided away from the ultrasound probe 2. As such a motion sensor 10, for example, although not shown, a known camera may be used to detect the position information of the ultrasound probe 2. The motion sensor 10 may detect the posture angle of the ultrasound probe 2 based on the detected position information on the ultrasound probe 2.

As an example of the movement amount of the ultrasound probe 2, the standard deviation of the posture angle of the ultrasound probe 2 has been described. However, the amount of change in the posture angle within a predetermined time, that is, a sum obtained by adding the posture angle differences between the ultrasound images of frames adjacent to each other in the order of time series within a predetermined time may be used as the movement amount of the ultrasound probe 2.

The movement amount of the ultrasound probe 2 is not limited to one using the posture angle of the ultrasound probe 2 as long as the movement amount indicates the movement of the ultrasound probe 2. For example, the movement amount of the ultrasound probe 2 may be the movement distance of the ultrasound probe 2.

The image analysis on the ultrasound image of a single frame in step S6 is not limited to the template matching described as an example. For example, the image analysis unit 12 can perform known analysis methods, such as pixel value analysis (for example, edge analysis), machine learning, and depth learning. For example, in a case where the edge analysis is performed as the image analysis in step S6, the image analysis unit 12 can calculate the area of pixels of the edge structure facing in a specific direction, for example, an oblique direction, in the ultrasound image. In this case, in step S7, the part determination unit 13 can determine the part included in the ultrasound image by determining whether or not the area of the edge structure calculated in step S6 is equal to or greater than a predetermined value.

The image analysis on the ultrasound image of a single frame in step S6 may fail due to the imaging conditions, and shaking of the ultrasound probe 2 at the time of transmission and reception of ultrasound beams, and the like. For this reason, in step S12, the image analysis unit 12 can perform image analysis for each frame on the ultrasound images of a plurality of frames acquired in time series and integrate the results of the plurality of image analyses. The image analysis unit 12 can use various methods as a method of integrating the results of a plurality of image analyses. For example, the image analysis unit 12 can use, as a final image analysis result, a maximum value or a median value of the score of the similarity in pattern recognition, such as template matching, and the area value in pixel value analysis on the edge structure. The image analysis unit 12 can also determine success and failure of image analysis. For example, for a plurality of ultrasound images, a score equal to or greater than a predetermined value can be given to an ultrasound image for which the image analysis result, such as the score of the similarity in pattern recognition and the area value in pixel value analysis, can be calculated, and a score less than the predetermined value can be given to an ultrasound image for which no image analysis result can be calculated. In a case where the average value or the median value of the plurality of given scores is equal to or greater than a predetermined value, the image analysis unit 12 can integrate the results of the plurality of image analyses. In a case where the average value or the median value of the plurality of scores given by the image analysis unit 12 is less than the predetermined value, the process may return to step S1, or the operation of the ultrasound diagnostic apparatus 1 may be ended after displaying an error message on the display unit 9.

In the image analysis using the optical flow described in step S12, a vector number indicating the movement of a characteristic pattern, which is calculated from ultrasound images of frames adjacent to each other in the order of time series, is calculated. In step S12, the vector number mapped in a plurality of frames can be time-integrated using a plurality of ultrasound images acquired in time series. That is, the image analysis unit 12 can calculate a time change in the vector number of (N−1) sets using (N−1) sets of ultrasound image pairs adjacent to each other in the order of time series among N ultrasound images acquired in time series, and integrate the time change in the vector number of (N−1) sets using the time from the ultrasound image of the first frame to the ultrasound image of the N-th frame, for example. In this case, in subsequent step S7, the part determination unit 13 can determine the part included in the ultrasound image by determining whether or not the integration value of the vector number calculated in step S12 is equal to or greater than a predetermined value.

In step S12, the image analysis unit 12 may perform image analysis other than the optical flow. For example, the image analysis unit 12 can calculate the movement amount of the same edge structure commonly included in the ultrasound images of a plurality of frames. In addition, for example, the image analysis unit 12 can calculate the movement amount of a structure having a predetermined brightness or higher in a region of interest common in the ultrasound images of a plurality of frames. In these cases, in subsequent step S7, the part determination unit 13 can determine the part included in the ultrasound image by determining whether or not the movement amount calculated in step S12 is equal to or greater than a predetermined value.

Undoubtedly, the image analysis unit 12 is not limited to the image analysis method described above, and may calculate the movement amount of the structure of the part commonly included in the ultrasound images of a plurality of frames using a known image analysis method.

The image generation unit 7 of the image acquisition unit 3 generates the B mode image signal from the reception signal output from the reception circuit 5, but may generate image signals other than the B mode image signal from the reception signal. For example, although not shown, in order to generate a motion mode (M mode) image signal, a color Doppler image signal, an elastic image signal, or a sound speed map signal from the reception signal, the B mode processing unit 19 of the image generation unit 7 may be replaced with a processing unit that generates the M mode image signal, the color Doppler image signal, the elastic image signal, or the sound speed map signal.

As described above, in a case where an image signal other than the B mode image signal is generated from the reception signal, image analysis according to the type of each image signal may be performed. For example, in a case where the M mode image signal is generated from the reception signal, the image analysis unit 12 may perform pattern recognition using template matching, texture analysis, machine learning, or the like, or may perform time series image analysis using the optical flow.

In addition, for example, in a case where the color Doppler image signal, the elastic image signal, or the sound speed signal is generated from the reception signal, the image analysis unit 12 can analyze color information included in each image signal.

Since the ultrasound diagnostic apparatus 1 described above is small, the ultrasound diagnostic apparatus 1 may be a portable ultrasound diagnostic apparatus that can be easily carried and used, or may be a stationary ultrasound diagnostic apparatus that is installed and used in an examination room or the like.

The ultrasound probe 2 is not particularly limited as long as it is possible to transmit and receive an ultrasound beam to and from the subject, and may be in the form of a sector type, a convex type, a linear type, a radial type, or the like.

While the ultrasound diagnostic apparatus according to the embodiment of the present invention has been described in detail, the present invention is not limited to the above-described embodiment, and various improvements and modifications may be made without departing from the scope and spirit of the present invention. In addition, the plurality of examples shown above can be appropriately used in combination.

EXPLANATION OF REFERENCES

1: ultrasound diagnostic apparatus
2: ultrasound probe
3: image acquisition unit
4: movement amount detection unit
5: reception circuit
6: transmission circuit
7: image generation unit
8: display control unit
9: display unit
10: motion sensor
11: probe movement amount calculation unit
12: image analysis unit
13: part determination unit
14: device control unit
15: operation unit 16: storage unit
17: amplification unit
18: A/D conversion unit
19: B mode processing unit
20: image processing unit

What is claimed is:

1. An ultrasound diagnostic apparatus, comprising:
an ultrasound probe;
a motion sensor configured to detect a motion or a position of the ultrasound probe; and
a processor configured to
   acquire an ultrasound image by transmitting an ultrasound beam from the ultrasound probe toward a subject and receiving an ultrasound beam reflected from the subject,
   analyze the ultrasound image; and
   calculate a movement amount of the ultrasound probe based on the motion or the position of the ultrasound probe detected by the motion sensor,
wherein the processor performs image analysis on an ultrasound image of a single frame in a case where the movement amount of the ultrasound probe is equal to or greater than a predetermined threshold value, and performs image analysis on ultrasound images of a plurality of frames in a case where the movement amount of the ultrasound probe is less than the predetermined threshold value.

2. The ultrasound diagnostic apparatus according to claim 1,
wherein the processor is further configured to perform image analysis including pattern recognition or pixel value analysis on the ultrasound image of the single frame as the image analysis on the ultrasound image of the single frame.

3. The ultrasound diagnostic apparatus according to claim 1,
wherein the processor is further configured to perform analysis on a movement of a specific pattern commonly included in the ultrasound images of the plurality of frames as the image analysis on the ultrasound images of the plurality of frames.

4. The ultrasound diagnostic apparatus according to claim 2,
wherein the processor is further configured to perform analysis on a movement of a specific pattern commonly included in the ultrasound images of the plurality of frames as the image analysis on the ultrasound images of the plurality of frames.

5. The ultrasound diagnostic apparatus according to claim 1,
wherein the processor is further configured to perform image analysis for each frame on the ultrasound images of the plurality of frames acquired in time series, as the image analysis on the ultrasound images of the plurality of frames, and integrate results of the image analyses.

6. The ultrasound diagnostic apparatus according to claim 2,
wherein the processor is further configured to perform image analysis for each frame on the ultrasound images of the plurality of frames acquired in time series, as the image analysis on the ultrasound images of the plurality of frames, and integrate results of the image analyses.

7. The ultrasound diagnostic apparatus according to claim 1,
wherein the processor is further configured to determine a part of the subject, which is included in each ultrasound image on which the image analysis has been performed, based on a result of the image analysis.

8. The ultrasound diagnostic apparatus according to claim 2,
wherein the processor is further configured to determine a part of the subject, which is included in each ultrasound image on which the image analysis has been performed, based on a result of the image analysis.

9. The ultrasound diagnostic apparatus according to claim 3,
wherein the processor is further configured to determine a part of the subject, which is included in each ultrasound image on which the image analysis has been performed, based on a result of the image analysis.

10. The ultrasound diagnostic apparatus according to claim 5,
wherein the processor is further configured to determine a part of the subject, which is included in each ultrasound image on which the image analysis has been performed, based on a result of the image analysis.

11. The ultrasound diagnostic apparatus according to claim 1,
wherein the motion sensor is attached to the ultrasound probe, and
wherein the motion sensor is configured to detect an acceleration, an angular speed, or a position of the ultrasound probe.

12. The ultrasound diagnostic apparatus according to claim 2,
wherein the motion sensor is attached to the ultrasound probe, and
wherein the motion sensor is configured to detect an acceleration, an angular speed, or a position of the ultrasound probe.

13. The ultrasound diagnostic apparatus according to claim 3,
wherein the motion sensor is attached to the ultrasound probe, and
wherein the motion sensor is configured to detect an acceleration, an angular speed, or a position of the ultrasound probe.

14. The ultrasound diagnostic apparatus according to claim 5,
wherein the motion sensor is attached to the ultrasound probe, and
wherein the motion sensor is configured to detect an acceleration, an angular speed, or a position of the ultrasound probe.

15. The ultrasound diagnostic apparatus according to claim 1,
wherein the motion sensor is provided away from the ultrasound probe, and
wherein the motion sensor is configured to detect a position of the ultrasound probe.

16. The ultrasound diagnostic apparatus according to claim 2,
wherein the motion sensor is provided away from the ultrasound probe, and
wherein the motion sensor is configured to detect a position of the ultrasound probe.

17. The ultrasound diagnostic apparatus according to claim 3,
wherein the motion sensor is provided away from the ultrasound probe, and
wherein the motion sensor is configured to detect a position of the ultrasound probe.

18. The ultrasound diagnostic apparatus according to claim 5,
  wherein the motion sensor is away from the ultrasound probe, and
  wherein the motion sensor is configured to detect a position of the ultrasound probe.

19. A control method of an ultrasound diagnostic apparatus, comprising:
  acquiring an ultrasound image by transmitting an ultrasound beam from an ultrasound probe toward a subject and receiving an ultrasound beam reflected from the subject;
  detecting, with a motion sensor, a motion or a position of the ultrasound probe;
  performing image analysis, with a processor, on the acquired ultrasound image; and
  calculating, with the processor, a movement amount of the ultrasound probe based on the motion or the position of the ultrasound probe,
  wherein image analysis is performed on an ultrasound image of a single frame in a case where the movement amount of the ultrasound probe is equal to or great than a predetermined threshold value, and image analysis is performed on ultrasound images of a plurality of frames in a case where the movement amount of the ultrasound probe is less than the predetermined threshold value.

* * * * *